(12) United States Patent
Song et al.

(10) Patent No.: US 8,545,813 B2
(45) Date of Patent: Oct. 1, 2013

(54) PRE-TEMPLATED MACROMOLECULAR ARCHITECTURES WITH MULTIPLE GD(III) COMPLEXES AND METHODS OF USE AS MRI CONTRAST AGENTS

(75) Inventors: Ying Song, Wilmette, IL (US); Thomas J. Meade, Wilmette, IL (US); Ellen Kohlmeir, Naperville, IL (US)

(73) Assignee: Northwestern University, Evanston, IL (US)

( * ) Notice: Subject to any disclaimer, the term of this patent is extended or adjusted under 35 U.S.C. 154(b) by 720 days.

(21) Appl. No.: 12/359,914

(22) Filed: Jan. 26, 2009

(65) Prior Publication Data

US 2009/0196829 A1 Aug. 6, 2009

Related U.S. Application Data

(60) Provisional application No. 61/023,753, filed on Jan. 25, 2008.

(51) Int. Cl.
*A61B 5/055* (2006.01)

(52) U.S. Cl.
USPC ............................. 424/9.3; 424/9.35; 424/360

(58) Field of Classification Search
None
See application file for complete search history.

(56) References Cited

PUBLICATIONS

Huber et al. Bioconjugate chem. 1998, 242-249.*
Lee et al. Bull. Korean Chem. Soc. 2005, 833-836.*
Perez-Balderas et al. Org. Lett. 2003, 1951-1954.*
Hoogenboom et al. Chem. Commun. 2006, 4010-4012.*
Aime S. et al., "b-Cyclodextrin adducts of Gd(III) chelates: useful models for investigating the structural and dynamic determinants of the relaxivity of gadolinium-based systems" 2003 Mag. Reson. Chem. 41 800-805.
Aime S. et al., "New paramagnetic supramolecular adducts for MRI applications based on non-covalent interactions between Gd(III)-complexes and beta- or gamma-cyclodextrin units anchored to chitosan." 2006 J. Inorg. Biochem. 100 931-938.
Aime S., "Novel radical-responsive MRI contrast agent based on paramagnetic liposomes" 2003 Mag. Reson.Chem. 41 pp. 585-588.
Barge A. et al., "New CD derivatives as self-assembling contrast agents for magnetic resonance imaging (MRI)" 2007 J. Incl. Phenom. Macrocycl. Chem. 57 489-495.
Dirksen A. et al., "A supramolecular approach to multivalent target-specific MRI contrast agents for angiogenesis." 2005 Chem. Comm. pp. 2811-2813.
Gilbert E. et al., "Evaluation of a New Organic Azide: Hexakis(azidomethyl)benzene (HAB)" 1989 Propellants, Explosives, Pyrotechnics 14 19-23.
Hueber M. et al., "Fluorescently Detectable Magnetic Resonance Imaging Agents" 1998 Bioconjugate Chem. 9 pp. 242-249.
Modo M., "The in vitro effects of a bimodal contrast agent on cellular functions and relaxometry." 2007 NMR Biomed. 20 pp. 77-89.
Paris et al., "Auto-assembling of ditopic macrocyclic lanthanide chelates with transition-metal ions. Rigid multimetallic high relaxivity contrast agents for magnetic resonance imaging." 2006 Inorg. Chem. 45 pp. 5092-5102.
Prasuhn D.E. et al., "Viral MRI contrast agents: coordination of Gd by native virions and attachment of Gd complexes by azide-alkyne cycloaddition" 2007 Chem. Commun. 1269-1271.
Rostovtsev V. et al., "A Stepwise Huisgen Cycloaddition Process: Copper(I)-Catalyzed Regioselective Ligation of Azides and Terminal Alkynes" 2002 Angew. Chem. Intl. Ed. 41 2596-2599.
Rudovsky et al., "PAMAM Dendrimeric Conjugates with a Gd-DOTA Phosphinate Derivative and Their Adducts with Polyaminoacids: The Interplay of Global Motion, Internal Rotation, and Fast Water Exchange" 2006 Bioconjugate Chem. 17 pp. 975-987.
Torres et al., "Supramolecular Assembly of an Amphiphilic GdIII Chelate: Tuning the Reorientational Correlation Time and the Water Exchange Rate" 2006 E. Chem Eur. J. 12 pp. 940-948.
Viguier R. et al., "A sensitized europium complex generated by micromolar concentrations of copper(I): toward the detection of copper(I) in biology." 2006 J. Am. Chem. Soc. 128 11370-11371.
Zong Y. et al., "Effect of size and charge on pharmacokinetics and in vivo MRI contrast enhancement of biodegradable polydisulfide Gd(III) complexes." 2006 Controlled Release 112 pp. 350-356.

* cited by examiner

*Primary Examiner* — Michael G Hartley
*Assistant Examiner* — Sean R Donohue
(74) *Attorney, Agent, or Firm* — Casimir Jones SC

(57) ABSTRACT

The present invention relates to contrast agents for MRI and related methods of use.

2 Claims, 14 Drawing Sheets

R= t-Bu

PRE-TEMPLATED MACROMOLECULAR ARCHITECTURES WITH MULTIPLE GD(III) COMPLEXES AND METHODS OF USE AS MRI CONTRAST AGENTS

CROSS-REFERENCE TO RELATED APPLICATION

This application claims priority to pending U.S. Provisional Patent Application No. 61/023,753 filed Jan. 25, 2008 herein incorporated by reference in its entirety.

STATEMENT REGARDING FEDERALLY SPONSORED RESEARCH OR DEVELOPMENT

This invention was made with government support under Grant Nos. CA090810 and CA119341 awarded by the National Institutes of Health. The government has certain rights in the invention.

FIELD OF THE INVENTION

The present invention relates to contrast agents for MRI and related methods of use.

BACKGROUND

Improved magnetic resonance (MR) contrasting agents are needed.

SUMMARY

The present invention relates to contrast agents for MRI and related methods of use. In certain embodiments, the present invention provides new MR contrast agents via click chemistry with various number of Gd(III) complexes covalently attached to the substrates. The simplicity of the synthesis and resulting high relaxivity render this approach attractive. The biocompatibility assays and the demonstration of efficient cell labeling show that these agents facilitate in vivo cell tracking by MRI.

In certain embodiments, the present invention provides compositions comprising at least one MR contrast agent with at least one covalently attached Gd(III) complex synthesized via click chemistry. The compositions are not limited to a particular type of click chemistry. In some embodiments, the click chemistry is a copper(I) catalyzed [3+2]cycloaddition reaction. The compositions are not limited to a particular type of MR contrast agent. In some embodiments, the MR contrast agent is, for example,

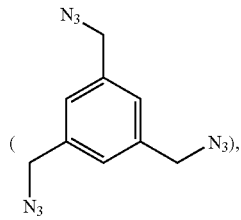

compound 1

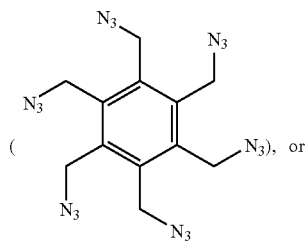

2

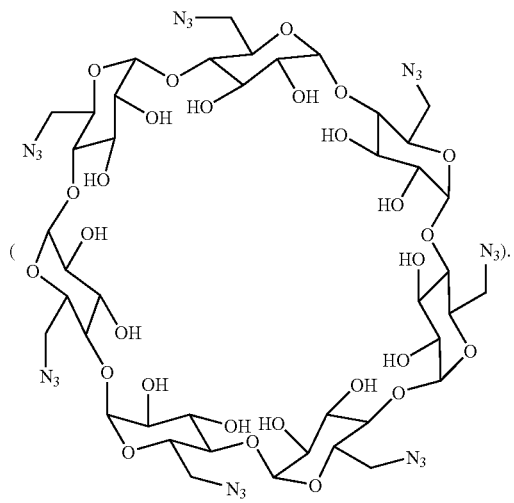

3

In some embodiments, the MR contrast agent is 4

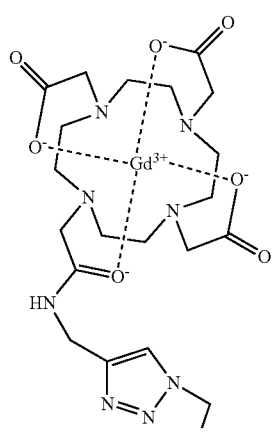

4

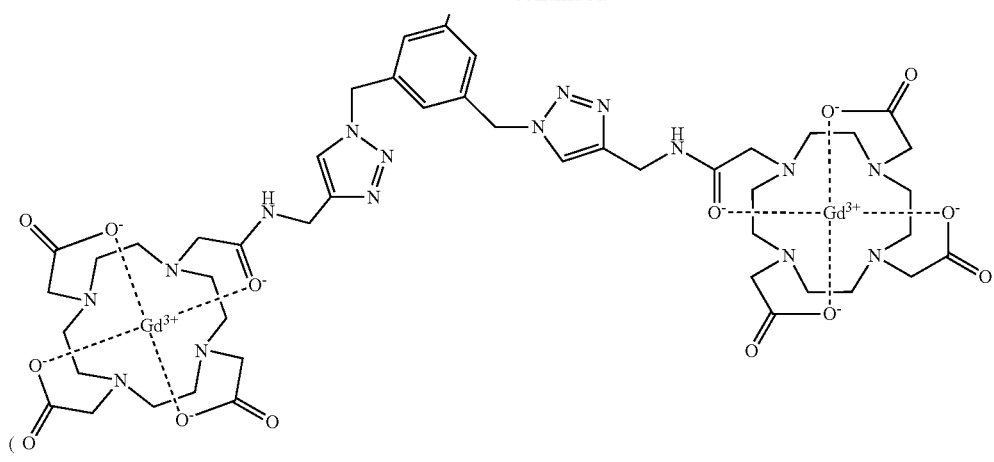
),
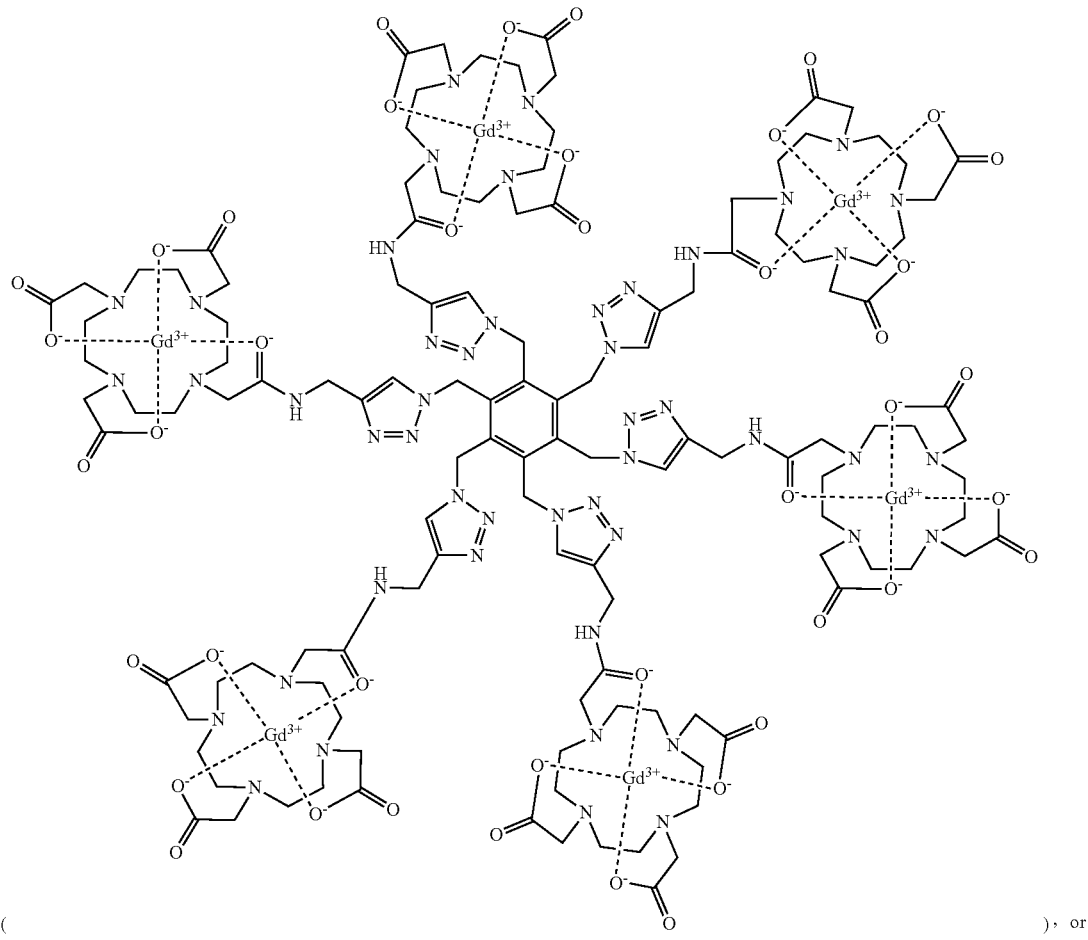
), or

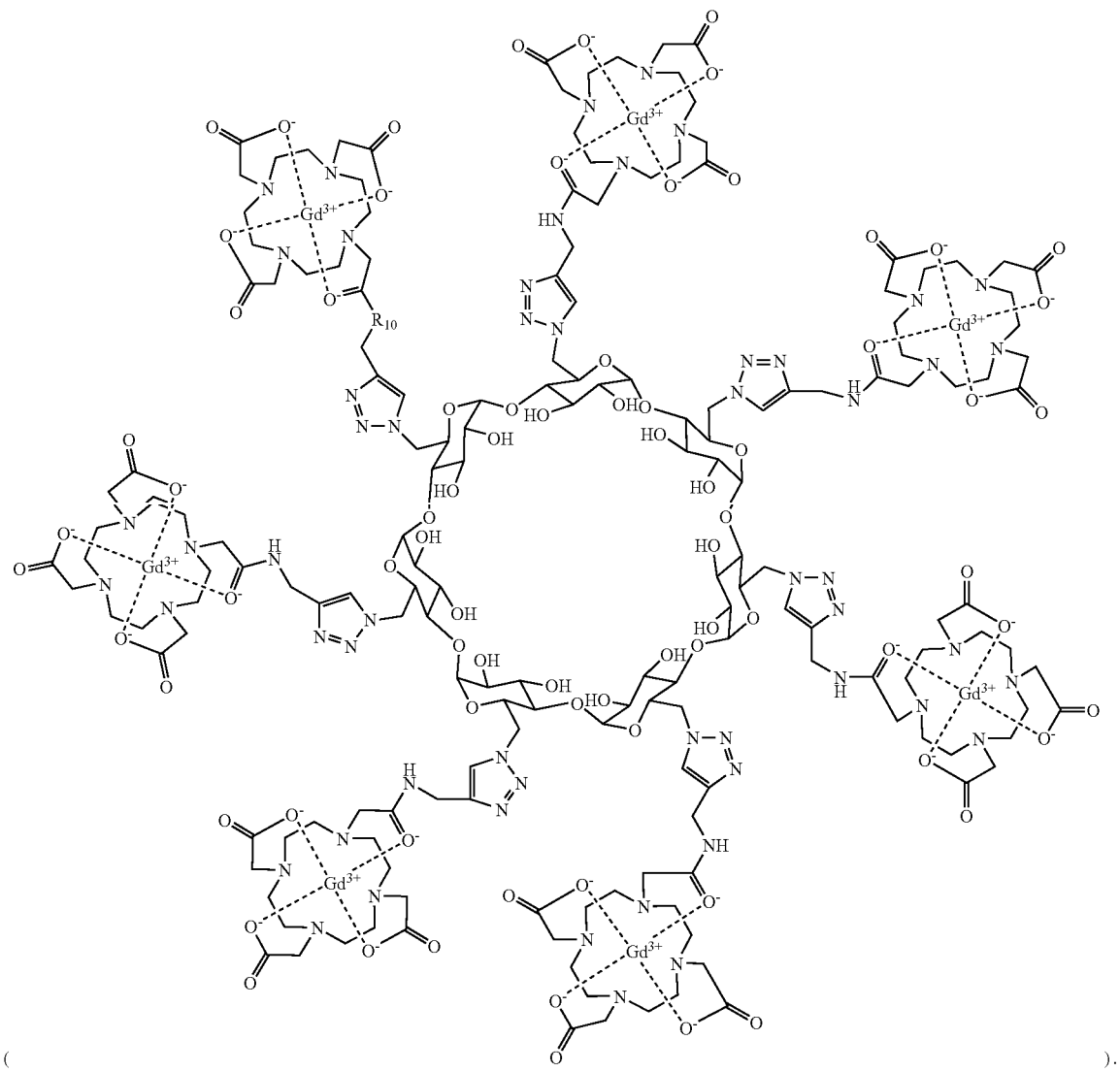

(                                                                                                              ).

In certain embodiments, the present invention provides methods of imaging (e.g., MR imaging) comprising introducing compositions comprising at least one MR contrast agent with at least one covalently attached Gd(III) complex synthesized via click chemistry to a cell, tissue, or organism and detecting said contrasting agent.

DETAILED DESCRIPTION

Figure 1:
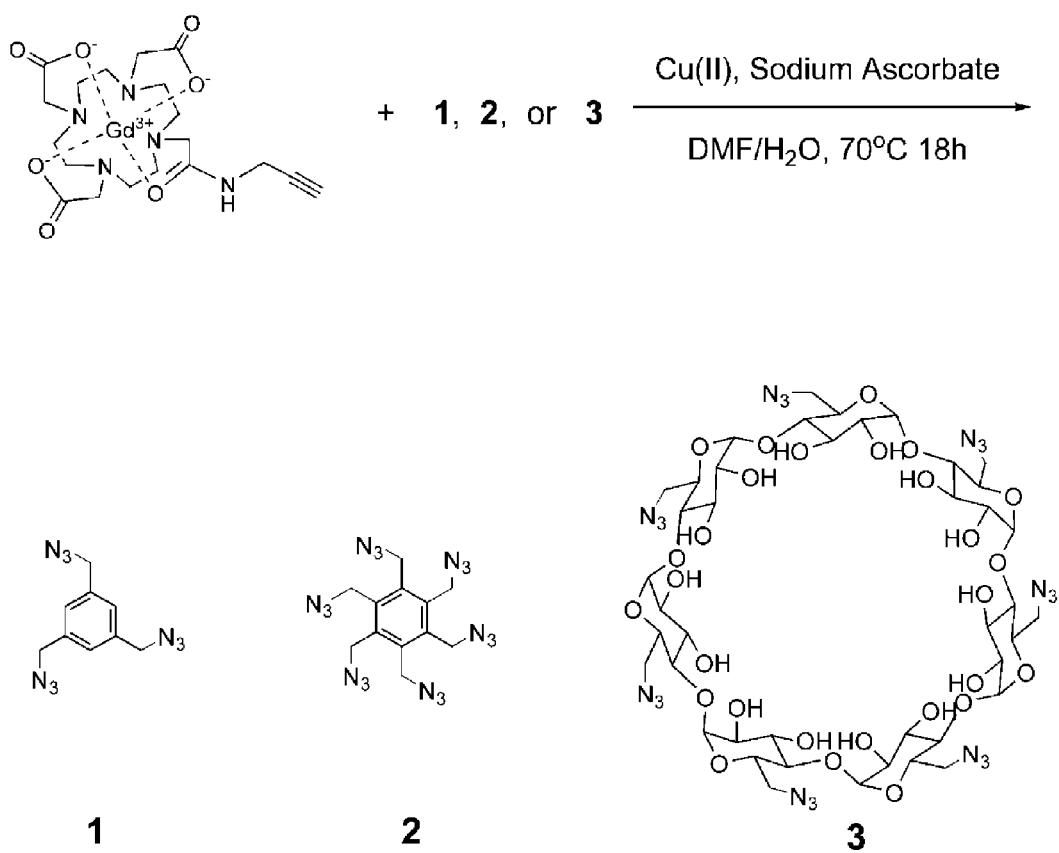
FIG. 1 shows the synthetic scheme of high-relaxivity MR contrast agents via click chemistry.
Figure 1:
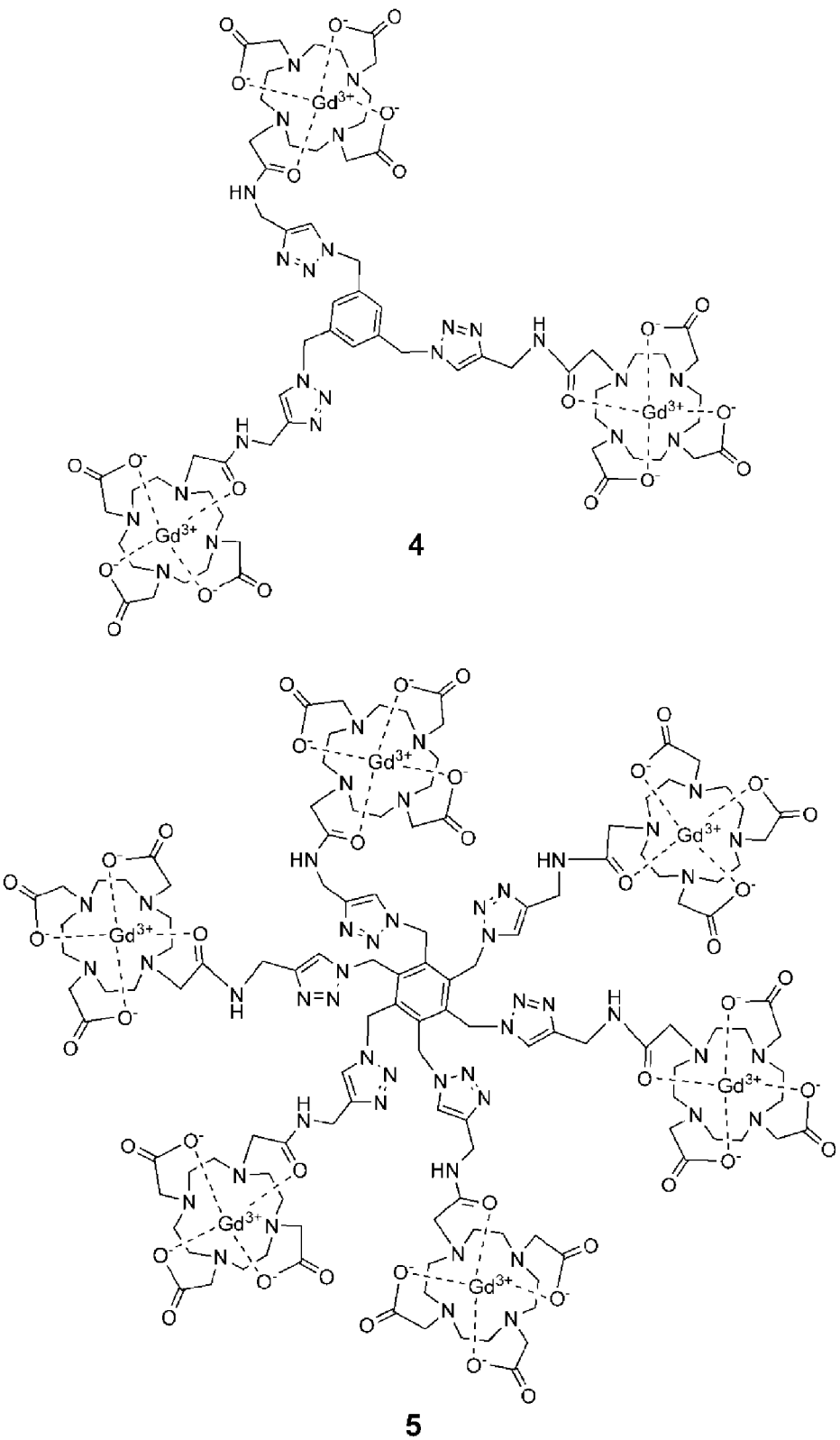
Figure 1:
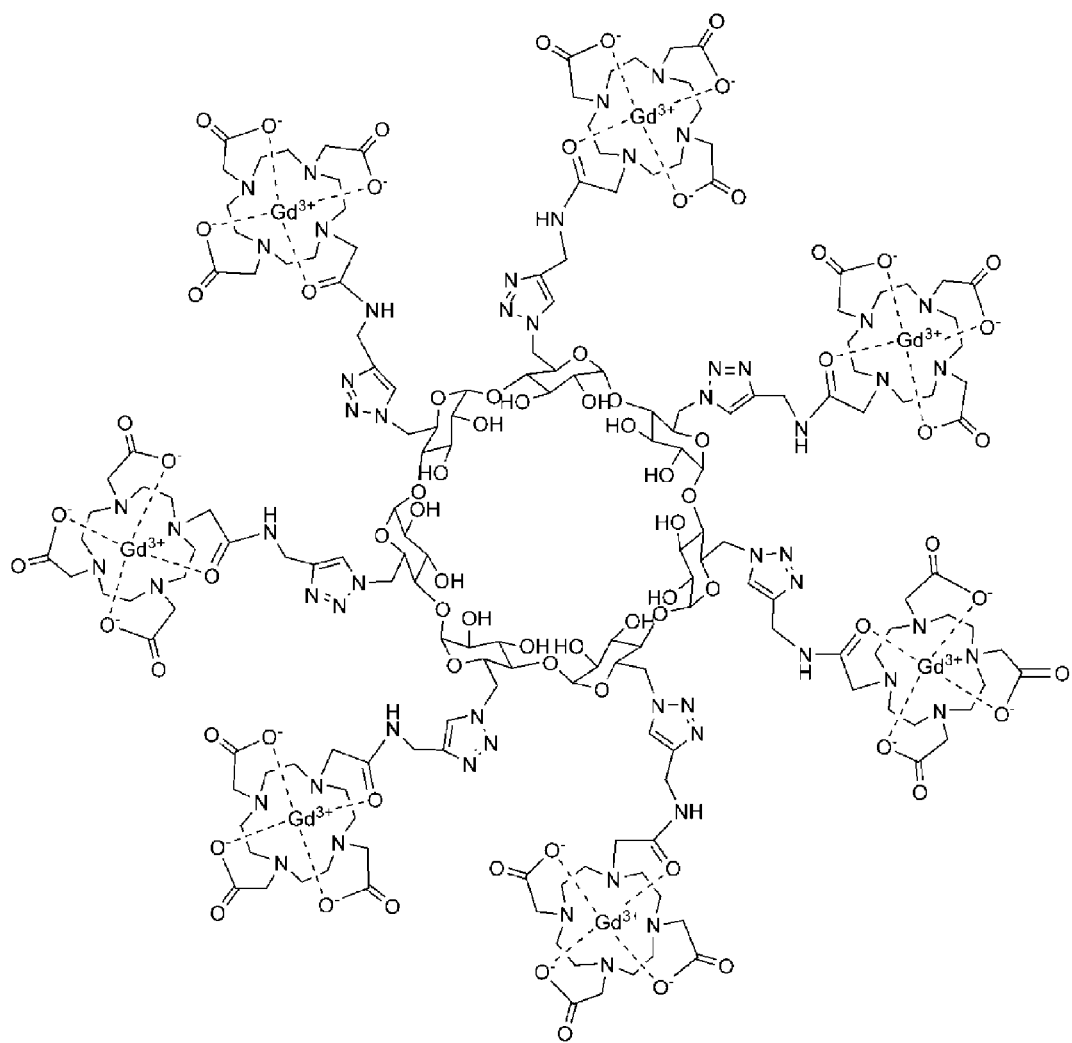

Advances in magnetic resonance imaging (MRI) have extended the application of this technique from routine clinical diagnosis toward cellular imaging (see, e.g., Modo, M. M.; Bulte, J. W. W; Eds. Molecular and Cellular MR Imaging, CRC Press: Boca Raton, Fla. 2007; Voisin, P.; Ribot, E. J.; Miraux, S.; Bouzier-Sore, A.-K.; Lahitte, J.-F.; Bouchaud, V.;

Mornet, S.; Thiaudiere, E.; Franconi, J.-M.; Raison, L.; Labrugere, C.; Delville, M.-H. Bioconjugate Chem. 2007, 18, 1053-1063; Frullano, L.; Meade, T. J. J. Biol. Inorg. Chem. 2007, 12, 939-949; each herein incorporated by reference in their entireties). Gd(III) complexes are used in MR imaging to enhance local contrast. Gd(III) ions reduce the longitudinal relaxation time ($T_1$) of surrounding water protons rendering an increase in signal intensity in an appropriately weighted MR image.

The lack of sensitivity of Gd(III) MR contrast agents limits the resolution and application of MR in cellular imaging in comparison with contrast agents for positron emissive tomography (PET) and light microscopy (see, e.g., Brekke, C.; Morgan, S. C.; Lowe, A. S.; Meade, T. J.; Price, J.; Williams, S. C. R.; Modo, M. NMR Biomed. 2007, 20, 77-89; herein incorporated by reference in its entirety). The Solomon-Bloembergen-Morgan theory predicts an increase in rotational correlation time ($\tau_R$) of a contrast agent will have a dramatic effect on the observed relaxivity (see, e.g., Merbach, A. E.; Toth, E. Eds The Chemistry of Contrast Agents in Medical Magnetic Resonance Imaging, Wiley: New York. 2001; herein incorporated by reference in its entirety). Typically, an increase in molecular weight slows down the rotation of the Gd(III) complex and therefore increases its relaxivity.

Strategies for Gd(III) amplification include self-assembly of multiple Gd(III) complexes into liposomes (see, e.g., Glogard, C.; Stensrud, G.; Aime, S. Mag. Reson. Chem. 2003, 41, 585-588; herein incorporated by reference in its entirety), micelles (see, e.g., Torres, S.; Martins, J. A.; Andre, J. P.; Geraldes, C. F.; G; C; Merbach, A. E.; Toth, E. Chem. Eur. J. 2006, 12, 940-948; herein incorporated by reference in its entirety), clusters (see, e.g., Paris, J.; Gameiro, C.; Humblet, V.; Mohapatra, P. K.; Jacques, V.; Desreux, J. F. Inorg. Chem. 2006, 45, 5092-5102; Livramento, J. B.; Toth, E.; Sour, A.; Borel, A.; Merbach, A. E.; Ruloff, R. Angew. Chem., Intl. Ed. 2005, 44, 1480-1484; each herein incorporated by reference in their entireties), or conjugation to polymers (see, e.g., Zong, Y.; Guo, J.; Ke, T.; Aaron, M. M; Parker, D. L.; Lu, Z.-R. J. controlled release 2006, 112, 350-356; Allen, M. J.; Raines, R. T.; Kiessling, L. L. J. Am. Chem. Soc. 2006, 128, 6534-6535; each herein incorporated by reference in their entireties), dendrimers (see, e.g., Lebduskova, P.; Sour, A.; Helm, L.; Toth, E.; Kotek, J.; Lukes, I.; Merbach, A. E. Dalton Trans. 2006, 3399-3406; Rudovsky, J.; Botta, M.; Hermann, P.; Hardcastle, K. I.; Lukes, I.; Aime, S. Bioconjugate Chem. 2006, 17, 975-987; each herein incorporated by reference in their entireties), biomacromolecules and scaffolds (see, e.g., Anderson; E. A.; Isaacman, S.; Peabody, D. S.; Wang, E. Y.; Canary, J. W.; Kirshenbaum, K. Nano Lett. 2006, 6, 1160-1164; Dirksen, A.; Langereis, S.; de Waal, B. F, M.; van Genderen, M. H. P; Hackeng; T. M.; Meijer, E. W. Chem. Comm. 2005, 2811-2813; each herein incorporated by reference in their entireties). Previous research has demonstrated an ability to track Gd(III) labeled cells in vivo with a polymeric contrast agent Gd-DTPA-tetramethylrhodamine-aminedextran (GRID) (see, e.g., Hueber, M. M.; Staubli, A. B.; Kustedjo, K.; Gray, M. H. B; Shih, J.; Fraser, S. E.; Jacobs, R. E.; Meade, T. J. Bioconjugate Chem. 1998, 9, 242-249; herein incorporated by reference in its entirety). However, the synthesis of GRID results in a mixture of polydispersed molecular weights which are difficult to characterize. In addition, unreacted amines on the polymer backbone contribute to cellular toxicity, limiting the incubation concentration and exposure time for cell labeling.

The present invention provides an efficient, inexpensive approach to prepare new MR contrast agents of high molecular relaxivity with multiple Gd(III) complexes. In experiments conducted during the course of development of embodiments for the present invention, click chemistry was employed to generate pre-templated macromolecular architectures with multiple Gd(III) complexes. The present invention is not limited to a particular type of cycloaddition reaction (click chemistry) in generating pre-templated macromolecular architectures with multiple Gd(III) complexes. In some embodiments, the copper(I) catalyzed [3+2] cycloaddition reaction is used in generating pre-templated macromolecular architectures with multiple Gd(III) complexes. Indeed, copper(I) catalyzed [3+2]cycloaddition reaction between an azide substrate and a terminal alkyne is regiospecific and compatible with a wide range of reaction conditions (see, e.g., Rostovtsev, V. V.; Green, L. G.; Fokin, V. V.; Sharpless, B. K. Angew. Chem., Intl. Ed. 2002, 41, 2596-2599; herein incorporated by reference in its entirety). The resulting triazole ring structure covalently bonds the Gd(III) complexes to the substrates. The rigid nature of the triazole linker hinders the local rotation of the Gd(III) complexes and further enhances the relaxivity.

In some embodiments, templates with varying numbers of azides are used to construct contrast agents of different molecular. The present invention is not limited to particular templates. In some embodiments, three templates with varying numbers of azides present are used to construct contrast agents of different molecular weights. In some embodiments, benzene based substrates act as a template to attach 3 to 6 Gd(III) complexes, and for β-cyclodextrin (β3-CD) which has 7.

Gd-DOTA and Gd-DTPA derivatives non-covalently associate with β-CD and form inclusion complexes resulting in an increase in relaxivity (see, e.g., Aime, S.; Gianolio, E.; Uggeri, F.; Tagliapietra, S.; Barge, A.; Cravotto, G. J. Inorg. Biochem. 2006, 100, 931-938; Barge, A.; Cravotto, G.; Robaldo, B.; Gianolio, E.; Aime, S. J. Incl. Phenom. Macrocycl. Chem. 2007, 57, 489-495; each herein incorporated by reference in their entireties). However, each cyclodextrin molecule can host no more than one Gd(III) complex and the association constants are between $103\sim104$ $mol^{-1}$ (see, e.g., Aime, S.; Botta, M.; Gianolio, E.; Terreno, E. Angew. Chem. Intl. Ed. 2000, 39, 747-750; Aime, S.; Gianolio, E.; Terreno, E.; Menegotto, I.; Bracco, C.; Milone, L.; Cravotto, G. Mag. Reson. Chem. 2003, 41, 800-805; each herein incorporated by reference in their entireties). Covalent attachment of Gd(III) complexes to the surface of the β-CD prevents the dissociation of Gd(III) complexes from β-CD.

In experiments conducted during the course of development of the present invention, The Gd-DOTA-alkyne derivative was synthesized by modification of existing procedures (see, e.g., Prasuhn, D. E. Jr.; Yeh, R. M.; Obenaus, A.; Manchester, M.; Finn, M. G. Chem. Comm. 2007, 1269-1271; Viguier, R. F. H; Hulme, A. N. J. Am. Chem. Soc. 2006, 128, 11370-11371; each herein incorporated by reference in their entireties). Metallation of the DOTA-alkyne ligand was performed before the cycloaddition reaction because Cu(II) has a high affinity to the DOTA. The trismethylazido benzene, 1, heptismethylazido benzene, 2, and heptakis-6-azido-6-deoxy-β-cyclodextrin, 3, were synthesized from corresponding commercially available halides in one step. The azide compounds are known to be stable at room temperature (see, e.g., Gilbert, E. E.; Voreck, W. E. Propellants, Explosives, Pyrotechnics 1989, 14, 19-23; herein incorporated by reference in its entirety). Click chemistry was carried out in a water-dimethylformamide mixture with heating or under microwave irradiation. MALDI-MS characterization of complexes 4, 5, and 6 is consistent with expected products. FIG. 1 shows the structures for 1, 2, 3, 4, 5, and 6.

In experiments conducted during the course of development of the present invention, to evaluate the in vitro efficiency of the agents, $T_1$ relaxivity was measured on a Bruker Minispec 60 MHz relaxometer at 37° C. in nanopure water using a standard inversion-recovery pulse sequence. The relaxivity of Gd-DOTA-alkyne derivative was measured to be 3.21 mM$^{-1}$ s$^{-1}$, which is comparable to the reported value of Gd-DOTA. After conjugation with 1, 2, and 3, the measured relaxivities of the complexes increased dramatically and are summarized in Table 1. With an increase of the molecular weight and restricted rotation of the Gd chelates, the relaxivity per Gd(III) increased 2-4 fold. With various number of Gd(III) ions per molecule, the molecular relaxivities of the three new agents were significantly higher than commercially available agents, such as Dotarem (3.4 mM$^{-1}$ s$^{-1}$ at 64 MHz).

TABLE 1

Gd(III) ionic and molecular relaxivities of the new MRI contrast agents 4, 5, and 6 at 60 MHz, 37° C.

| Compounds | MW (g/mol) | Gd ionic $r_1$(mM$^{-1}$s$^{-1}$) | No. of Gd/Mol | Molecular $r_1$(mM$^{-1}$s$^{-1}$) |
|---|---|---|---|---|
| Gd-DOTA-alkyne derivative | 595.7 | 3.21 | 1 | 3.21 |
| 4 | 2030 | 5.90 ± 0.15 | 3 | 17.7 ± 0.47 |
| 5 | 3982 | 10.97 ± 0.13 | 6 | 65.8 ± 0.76 |
| 6 | 5480 | 12.20 ± 0.54 | 7 | 85.4 ± 3.74 |

Figure 2:
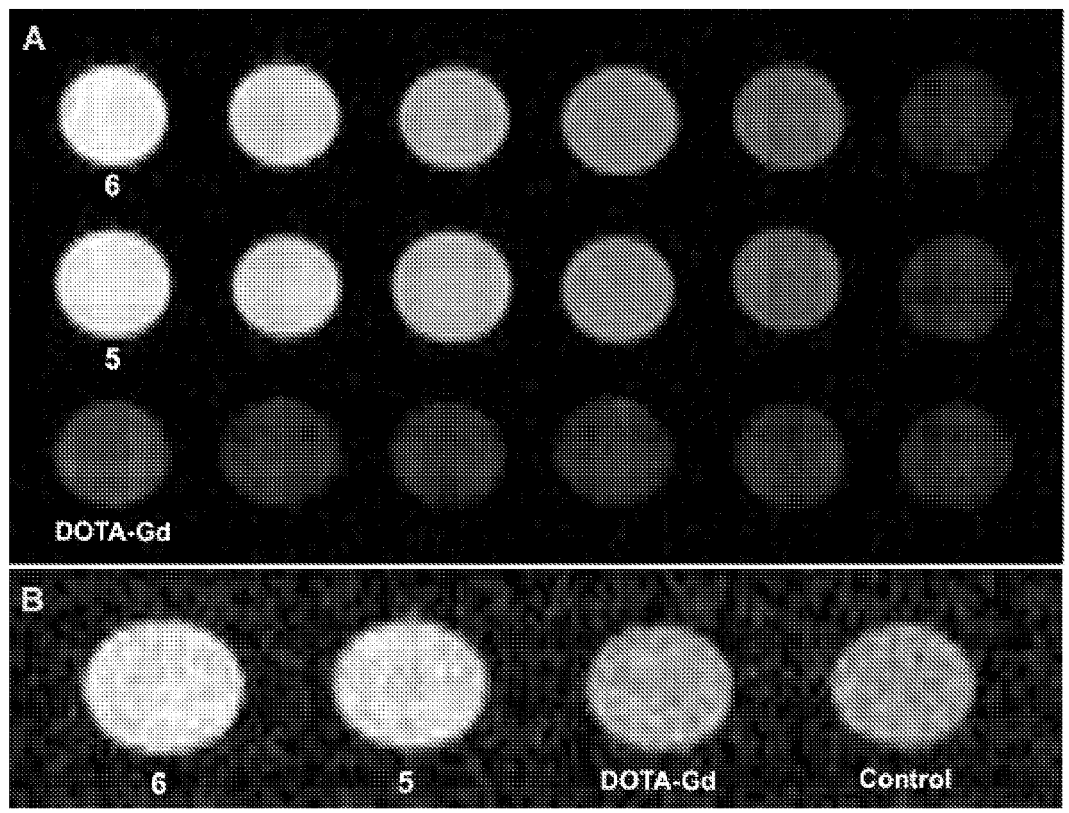
FIG. 2 shows A) Images of 5, 6 and Gd-DOTA in nanopure water at decreasing concentrations as follows from left to right for 6 (73.3, 54.9, 36.6, 22.0, 11.0, 0.0 μM) for 5 (82.1, 61.6, 41.0, 24.6, 12.3, 0.0 μM) and for Gd-DOTA (82.7, 62.0, 41.4, 24.8, 12.4, 0.0 μM). $T_1$ weighted ($T_R/T_E$=300/18.3 ms) spin-echo MRI phantom images at 200 MHz; and B) Images of pelleted NIH-3T3 cells incubated for 4 hours with 5, 6 and Gd-DOTA at equal molar concentrations of Gd(III) (7.8, 9.0, 9.0 mM Gd respectively). $T_1$ weighted ($T_R/T_E$=800/18.3 ms) spin-echo images were acquired at 200 MHz. Each sample diameter is 1 mm.
Figure 3:
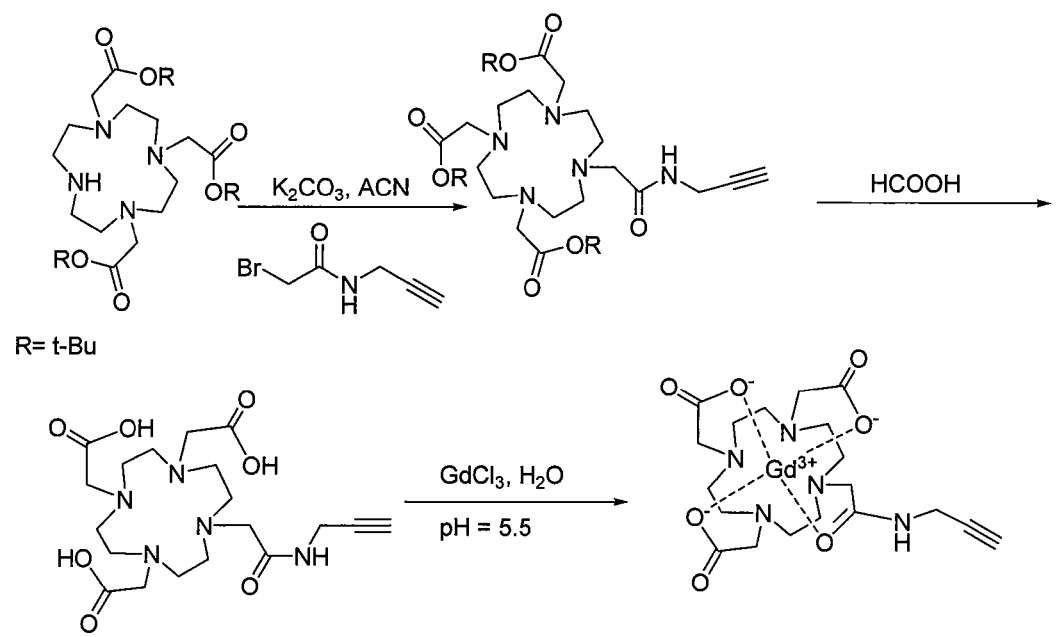
FIG. 3 shows synthesis scheme of Gd-DOTA alkyne derivative.
Figure 4:
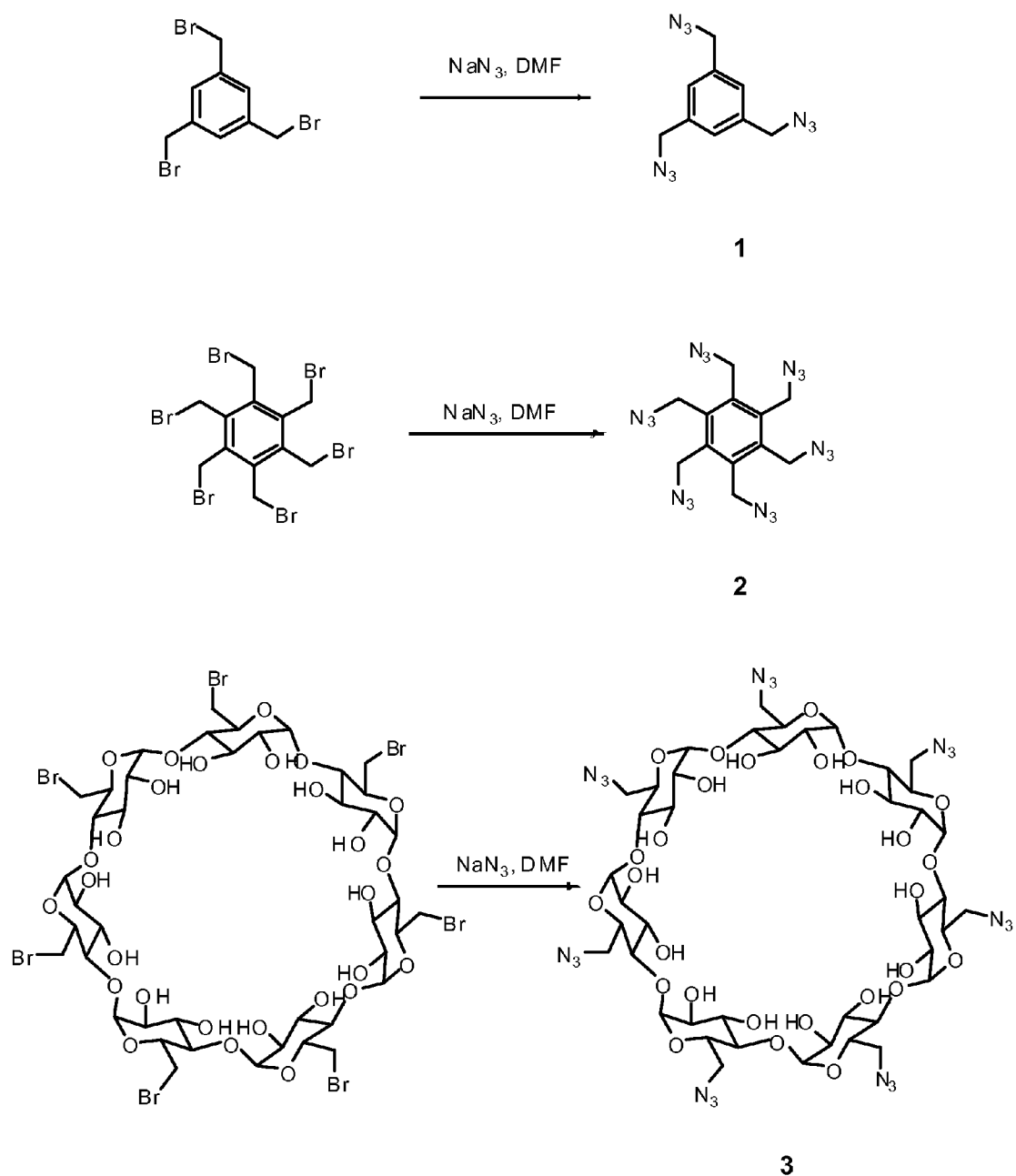
FIG. 4 shows synthesis of the poly azide substrates.

In experiments conducted during the course of development of the present invention, MR phantoms were imaged using a 4.7T, 200 MHz Bruker Biospec MR Imager with decreasing concentrations of 5, 6 and Gd-DOTA as indicated in FIG. 2A. $T_1$ measurements were obtained and relaxivities were calculated for each compound using the $T_1$ data. Relaxivities for 5, 6 and Gd-DOTA were calculated to be 5.3, 5.1, and 1.0 mM$^{-1}$ s$^{-1}$ at 200 MHz respectively. At high magnetic field strengths there remained a 5 fold increase in relaxivity per Gd(III) which indicated a 31-37 fold increase in molecular relaxivity.

In experiments conducted during the course of development of the present invention, 5 and 6 were used to label cells for MR imaging at equal molar concentrations of Gd(III) (FIG. 2B). Normalizing the incubation concentration of the agents according to Gd(III) ion accurately demonstrated the difference in efficacy of these new agents to effect image contrast. NIH-3T3 cells were incubated for 4 hours at 37° C. and 5% $CO_2$ in complete media containing 5, 6, and Gd-DOTA. The cells were rinsed 3 times in phosphate buffered saline and pelleted in 1 mm capillary tubes. Unlabeled cell pellets were used as a control. $T_1$ values measured for 5, 6, Gd-DOTA and the control cell pellet were 2067.7, 2178.4, 3009.4, and 3480.3 msec respectively. The images show, for example, that with a high relaxivity, 5 and 6 can effectively label cells at a lower incubation concentration and give a much brighter image.

In experiments conducted during the course of development of the present invention, 6 was further tested to measure the degree of cellular labeling and biocompatibility. Cells were labeled with increasing concentrations of 6 from 0.03 to 1.5 mM (0.2 to 10.2 mM Gd(III)) in complete media for 4 hours at 37° C. and 5% $CO_2$. A concentration dependant uptake profile was determined that saturated above 0.5 mM (4 mM Gd). Furthermore, cellular toxicity assays indicated a 98% viability with 6 up to 1.5 mM (10.2 mM Gd) for a 4 hour incubation.

Accordingly, in some embodiments, the present invention provides new MR contrast agents via click chemistry with various numbers of Gd(III) complexes covalently attached to the substrates. In some embodiments, the MR contrast agents are 4, 5, and 6. The simplicity of the synthesis and resulting high relaxivity render this approach attractive. The biocompatibility assays and the demonstration of efficient cell labeling show that these agents facilitate in vivo cell tracking by MRI.

EXAMPLES

The following examples are provided in order to demonstrate and further illustrate certain preferred embodiments and aspects of the present invention and are not to be construed as limiting the scope thereof.

1. Synthetic Procedures

Unless otherwise noted, materials and solvents were obtained from commercial suppliers and used without further purification. Doubly distilled deionized water was obtained from a NANO pure II filtration unit to 18 Ωcm resistivity. NMR spectra were obtained on a Varian Inova spectrometer at 500 mHz and a Varian Mercury spectrometer at 400 mHz. HPLC analyses were performed on a Varian Prepstar system for analysis and preparation (Varian Instruments Inc., USA) using a reverse phase HPLC column (Waters, Atlatantis C18).

a) Synthesis of Gd-DO3A Alkyne

Gd-DOTA alkyne derivative was synthesized after a modification of a literature procedure (see, e.g., Viguier, R. F. H.; Hulme, A. N. *J. Am. Chem. Soc.* 2006, 128, 11370-11371; Prasuhn, D. E.; Yeh, R. M.; Obenaus, A.; Manchester, M.; Fin, M. G. *Chem. Commun.*, 2007, 1269-1271; herein incorporated by reference in its entirety). Elemental analysis: Theory (M+5H$_2$O) C, 33.28; H, 5.24; N, 10.21; Found: C, 33.00; H, 5.42; N, 10.00; Relaxivity at 37° C., 60 mHz, nanopure H$_2$O: 3.21 mM$^{-1}$ s$^{-1}$; MS-ESI: 595 (with Gd isotope pattern).

b) General Procedure for the Synthesis of 1,3,5-tris(azidomethyl)benzene, 1, 1,2,3,4,5,6-hexakis(azidomethyl)benzene, 2 and β-CD azide 3.

The polyazides were synthesized in high yield from the known commercially available polybromides by nucleophilic substitution reaction with sodium azide according to literature (see, e.g., Gilber, E. E.; Voreck, W. E. Propellants, Explos.; Pyrotech. 1989, 14, 19; herein incorporated by reference in its entirety). Both the 1,3,5-tris(azidomethyl)benzene and 1,2,3,4,5,6-hexakis(azidomethyl)benzene were reported to be relatively insensitive to heat and shock (see, e.g., Prasuhn, D. E.; Yeh, R. M.; Obenaus, A.; Manchester, M.; Fin, M. G. Chem. Commun., 2007, 1269-1271; herein incorporated by reference in its entirety). However, organic azides are explosive materials and should be handled with care.

1,2,3,4,5,6-hexakis(azidomethyl)benzene 1:
white solid. $^1$H-NMR (d$^7$-DMF): 4.98 (s); $^{13}$C-NMR (d$^7$-DMF): 137.33; 47.98.

1,3,5-tris(azidomethyl)benzene 2:
pale yellow oil. $^1$H-NMR (CDCl$_3$): 7.22 (s, 3H); 4.36 (s, 6H), $^{13}$C-NMR (CDCl$_3$): 137.18, 127.71, 54.46.

β-CD azide 3:

white solid. $^1$H-NMR (d$^6$-DMSO): 5.87 (7H), 5.72 (7H), 4.86 (7H), 3.53-3.74, 3.31-3.29 (42H). $^{13}$C-NMR (d$^6$-DMSO): 102.67; 83.83; 73.23; 72.64, 70.96; 51.96. MALDI-MS: 13010. Mw: 1310.

c) General Procedure for Cu (I) Catalyzed Cycloaddition

Gd-DOTA alkyne derivative, Cu(II) sulfate (10 mol % per azide), sodium ascorbate (60 mol % per azide) and the azide substrate (1:1 azide mole ratio to Gd-DOTA alkyne) were dissolved in water/DMF 1:1 mixture and formed a cloudy solution. The reaction mixture was irradiated in a Biotag microwave for 5-20 min at 130° C., 4 bar or the reaction was heated in an oil bath at 70° C. overnight. For 6, after cooling down, the reaction mixture was loaded into a dialysis bag with MWCO 100 and dialyzed for 48 h against nanopure water. Future purification includes Chelex columns twice and a sephadex G25 column. For 4 and 5, reverse phase HPLC was used with water/acetonitrile gradient. Normally 50-60% yield was obtained.

2. Structure and Characterization of Three New MR Agents

Figure 5A:
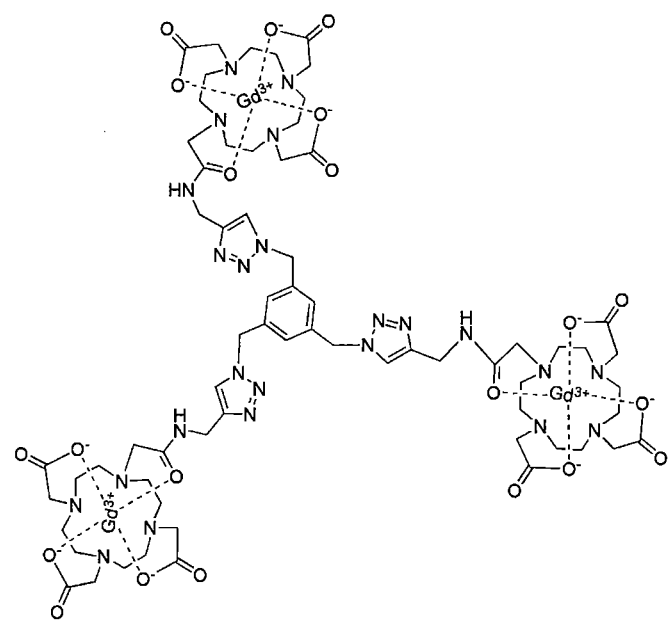
FIG. 5 shows the MALDI-MS of 4, Mw 2030.34.
Figure 5:
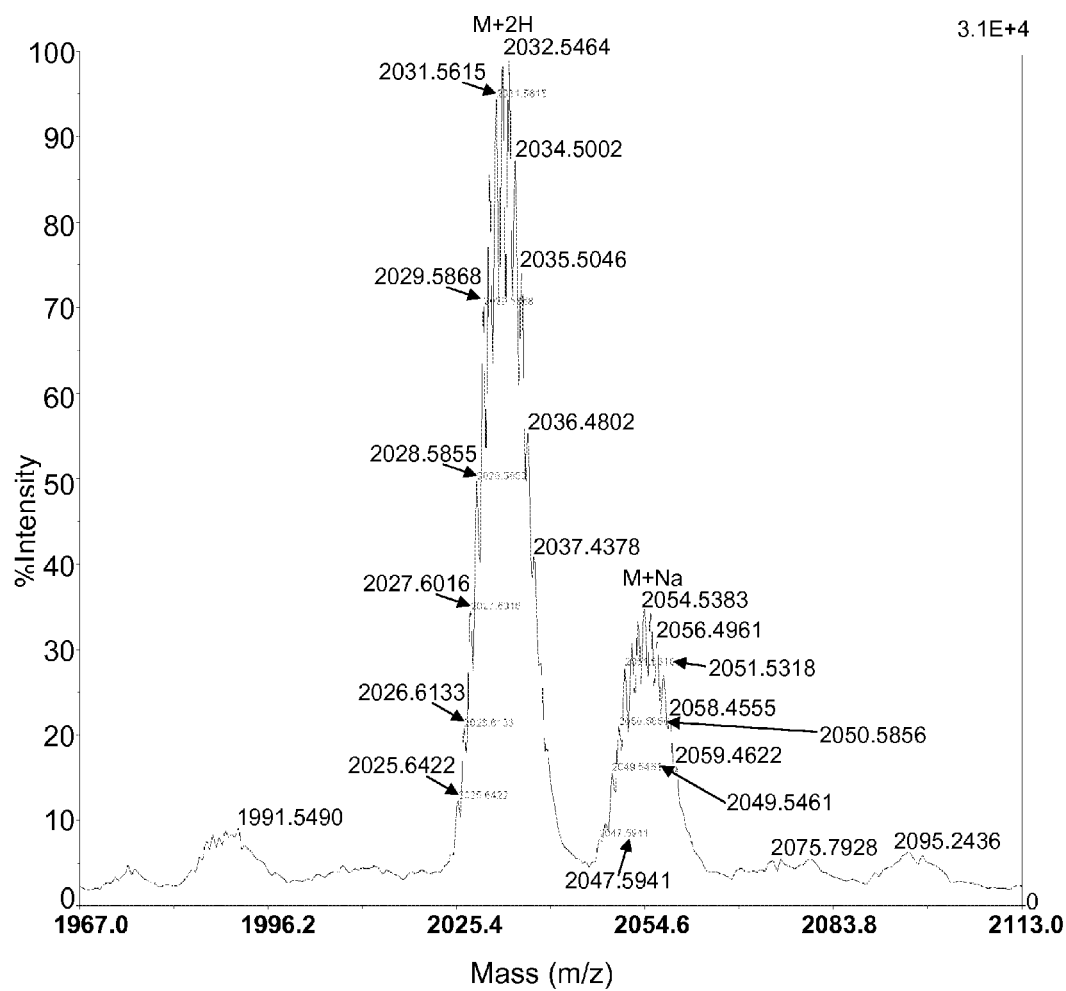
Figure 5:
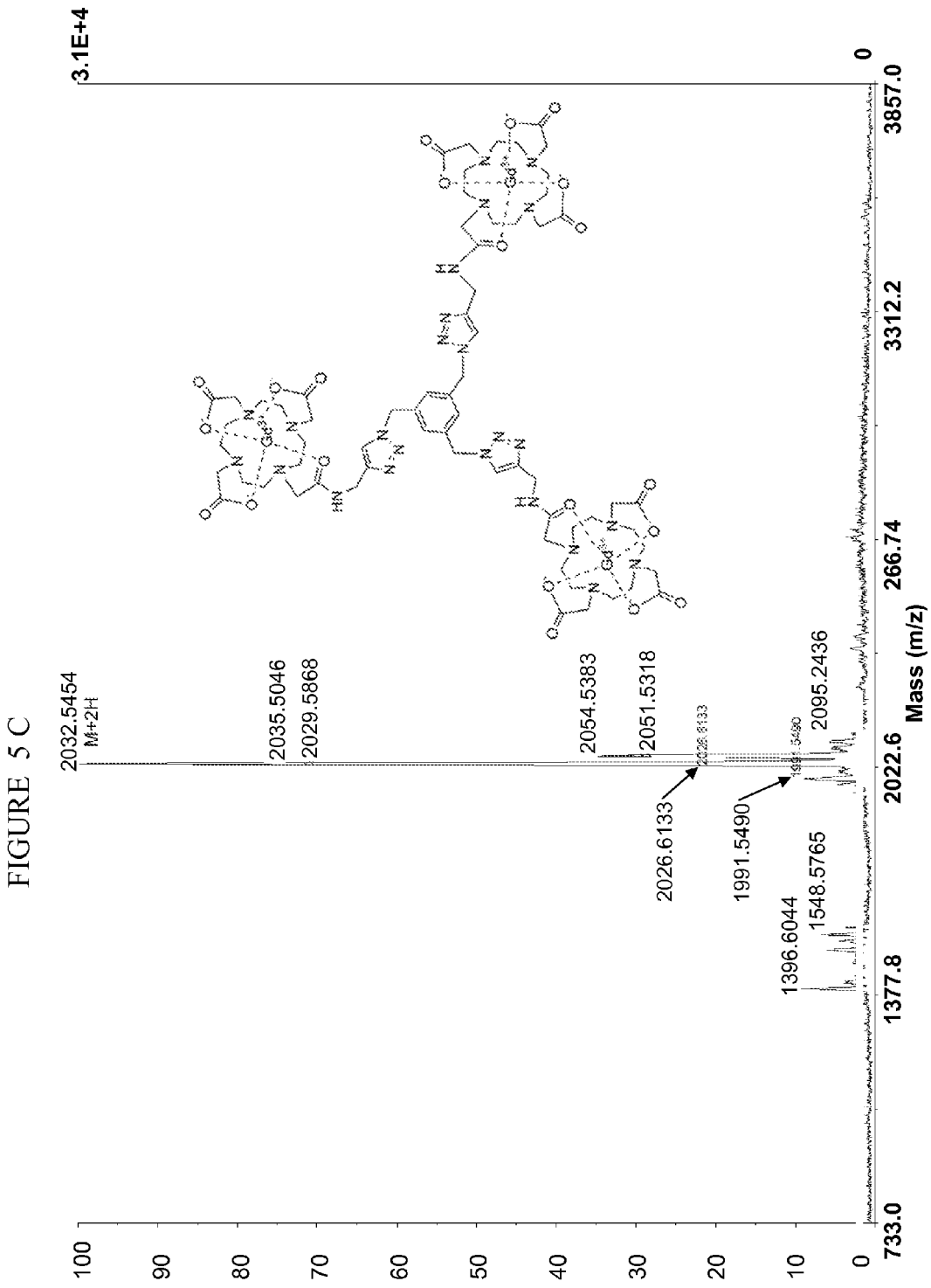

FIG. 5 shows the MALDI-MS of 4, Mw 2030.34.

Figure 6:
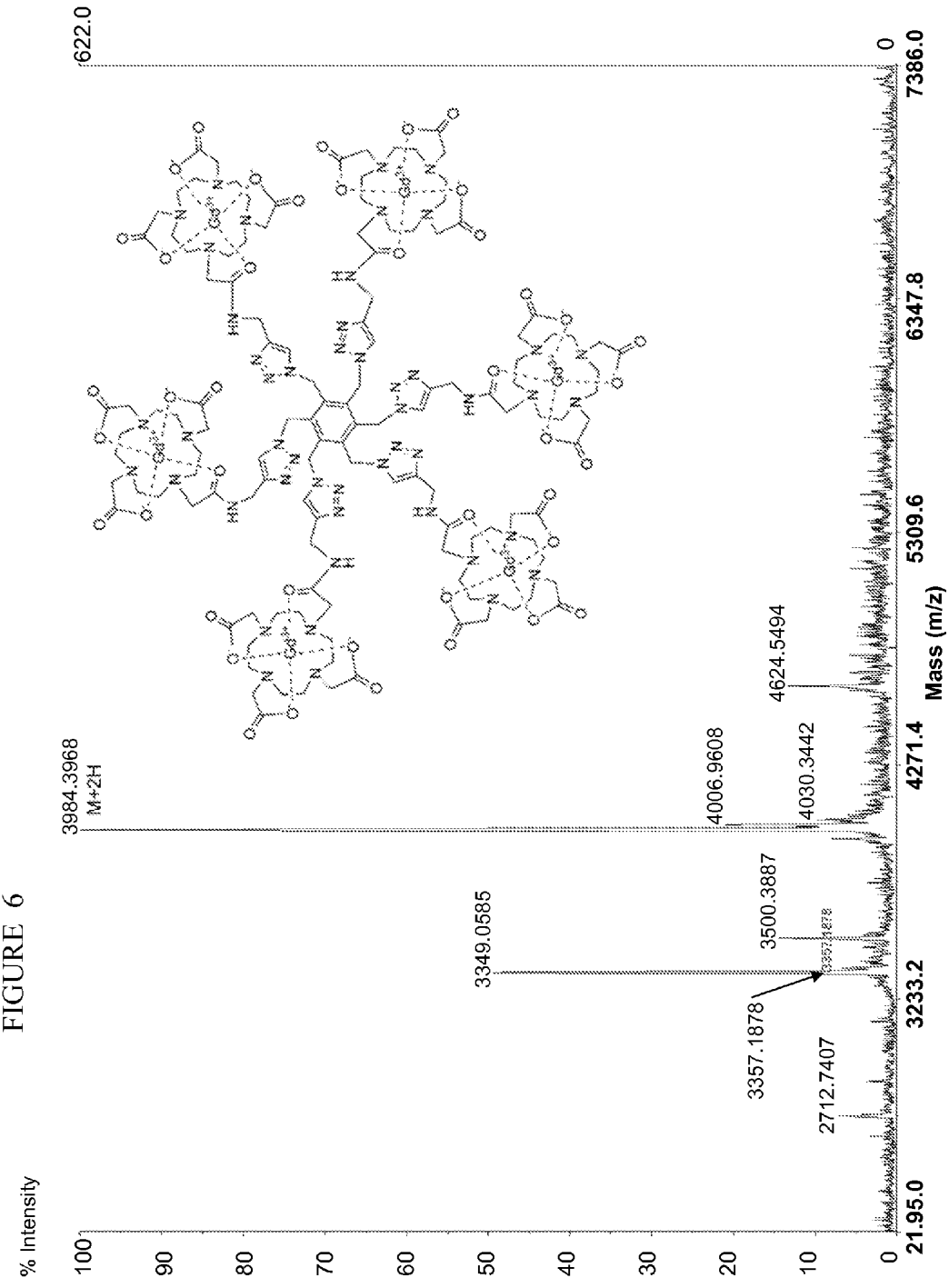
FIG. 6 shows the MALDI-MS of 5, Mw 3982.57.

FIG. 6 shows the MALDI-MS of 5, Mw 3982.57.

Figure 7:
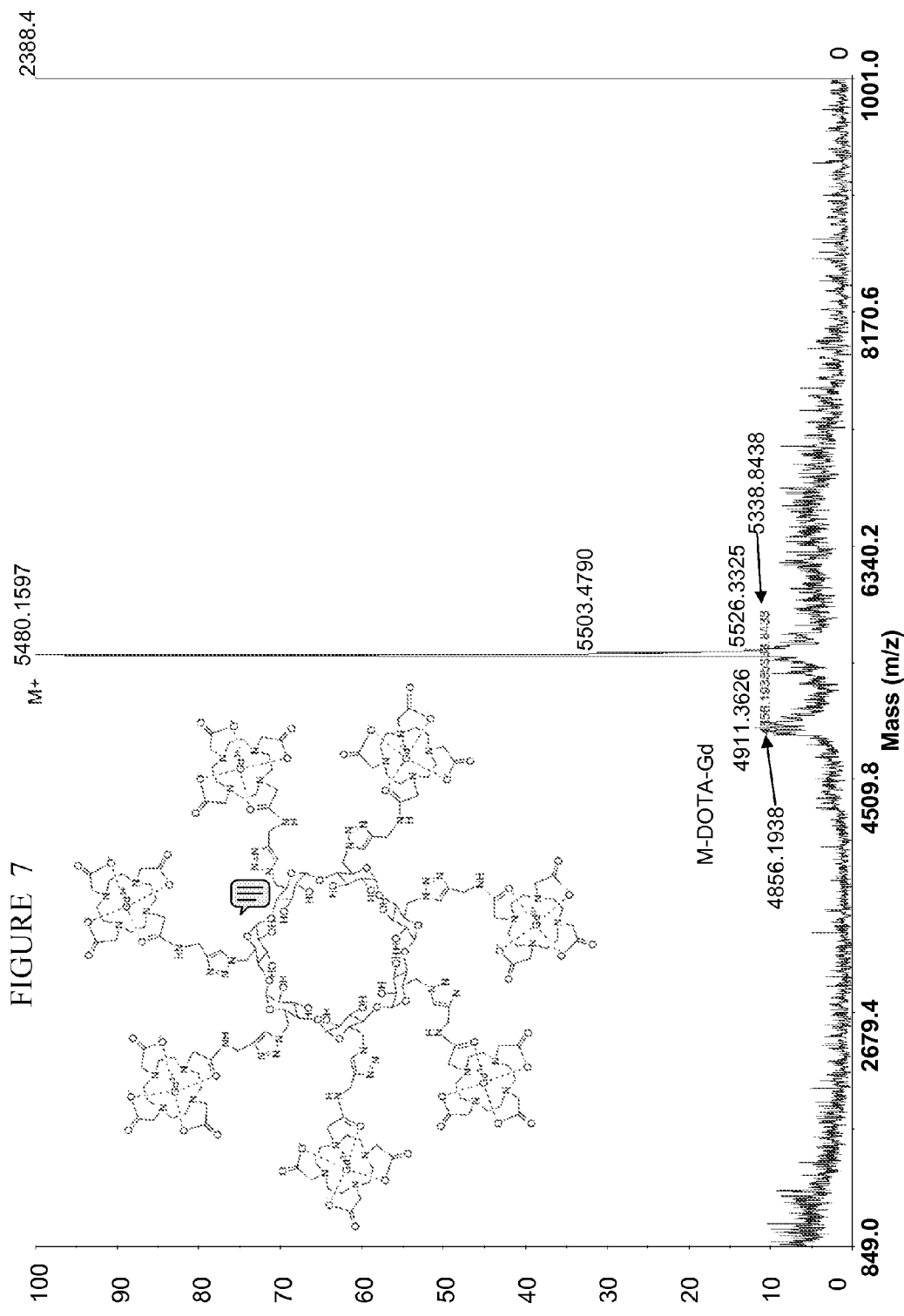
FIG. 7 shows the MALDI-MS of 6, Mw 5480.02.

FIG. 7 shows the MALDI-MS of 6, Mw 5480.02.

3. $T_1$ Measurement and Relaxivity of Agents in Solution 6, 5 and DOTA-Gd were dissolved in nanopure water at decreasing concentrations and imaged in 1 mm capillary tubes. Concentrations (μM) were as follows from left to right for 6 (73.3, 54.9, 36.6, 22.0, 11.0, 0.0) for 5 (82.1, 61.6, 41.0, 24.6, 12.3, 0.0) and for DOTA-Gd (82.7, 62.0, 41.4, 24.8, 12.4, 0.0). $T_1$ weighted ($T_R/T_E$=300/18.3 ms) spin-echo images were acquired at 200 MHz.

$T_1$ measurements were obtained by collecting a series of images using a standard spin-echo sequence with a $T_E$ of 8.2 ms and increasing $T_R$ (62, 100, 200, 300, 400, 500, 1000, 2500, 5000, 10000), 4 signal averages, FOV 2.3×2.3 cm, collected into a matrix of 128×128.

$T_1$ values were determined using the following equation.

$$S_I = S_0(1 - \exp_{R1}^{(-T/T)})$$

Where $S_I$ is the measured signal intensity for each $T_R$, $S_0$ is the signal intensity at infinity.

Relaxivities for each compound were calculated using the $T_1$ data and gadolinium concentrations as determined by ICP-MS analysis. A linear regression of $1/T_1$ (S$^{-1}$) vs. Gd concentration (mmol) gave a relaxivity of 5.3, 5.1, and 1.0 mM$^{-1}$ s$^{-1}$ for 6, 5 and DOTA-Gd respectively.

4. $T_1$ Measurement from $T_1$ Weighted Cell Pellet Images

Cell studies were done using NIH-3T3 cells cultured in Dulbecco's Modified Eagle's Media supplemented in 10% calf bovine serum and incubated at 37° C., 5% CO$_2$.

Cells were incubated with approximately equimolar concentrations of Gd for 4 hours in a 6 well plate. The cells were rinsed 2× with PBS and trypsinized. In 1.5 mL tubes, the cells were fixed for 15 min in 10% buffered neutral formalin and rinsed 2× in PBS. The cells were then pelleted in flame sealed 1 mm capillary tubes.

Figure 8:
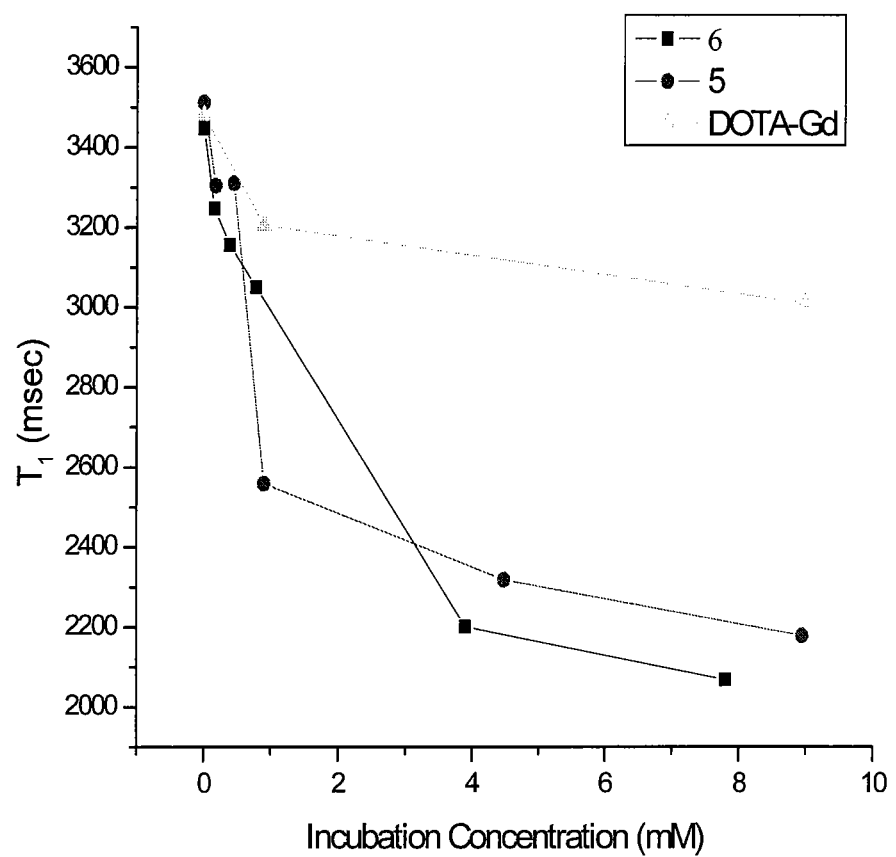
FIG. 8 shows $T_1$ time versus increasing incubation concentration of Gd(III) of Gd-DOTA, 5 and 6 compounds in NIH-3T3 cell pellets.

$T_1$ weighted ($T_R/T_E$=800/18.3 ms) spin-echo images were acquired at 200 MHz. $T_1$ measurements were obtained by collecting a series of images using a standard spin-echo sequence with a $T_E$ of 700 ms and a series of $T_R$ (91.5, 200, 300, 400, 500, 750, 1200, 2500, 5000, 10000), 6 signal averages, FOV 2×2 cm, collected into a matrix of 256×128. Table 2 summarizes the $T_1$ values for the highest concentration of incubation. FIG. 8 shows the relationship between $T_1$ and incubation concentration.

TABLE 2

$T_1$ values of 6, 5, and DOTA-Gd at approximately equimolar concentration of Gd(III).

|  | 6 | 5 | Gd-DOTA | Control |
|---|---|---|---|---|
| Incubation Concentration (mM Gd) | 7.80 | 8.95 | 9.00 | 0.00 |
| $T_1$ (msec) | 2067.73 | 2178.38 | 3009.44 | 3480.30 |
| % difference from control | 40.59 | 37.41 | 13.53 | 0.00 |

5. Cell Uptake and Viability Studies

Cell studies were performed to determine the ability for compound 6 to label cells. A mouse embryonic fibroblast cell line (NIH-3T3) was used. Cells were grown in Dulbecco's modified eagles media supplemented with 10% calf bovine serum at 37° C. and 5% CO$_2$. Cells were grown to 80% confluence in a 24 well cell culture plate at 400 uL per well. Media was then replaced with media containing increasing concentrations of 6 from 0-10.25 mM in triplicate. The plate was incubated for 4 hours and then washed two times with sterile phosphate buffered saline. Each sample was then trypsinized and tested for cell count and viability on a Guava PCA system using the Guava viacount protocol according to the manufacturer's instructions. The remaining volume in each sample was dissolved in concentrated nitric acid and diluted for analysis by inductively coupled plasma-mass spectrometry to determine the amount of Gadolinium associated with the cells.

Figure 9:
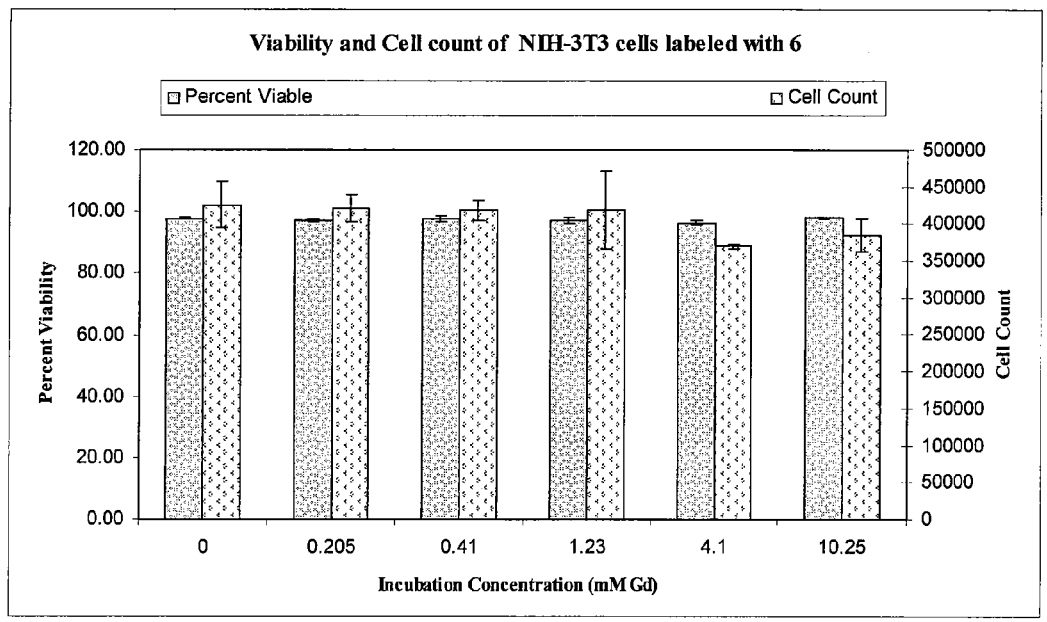
FIG. 9 shows viability and cell count of 6 labeled NIH-3T3 cells.
Figure 10:
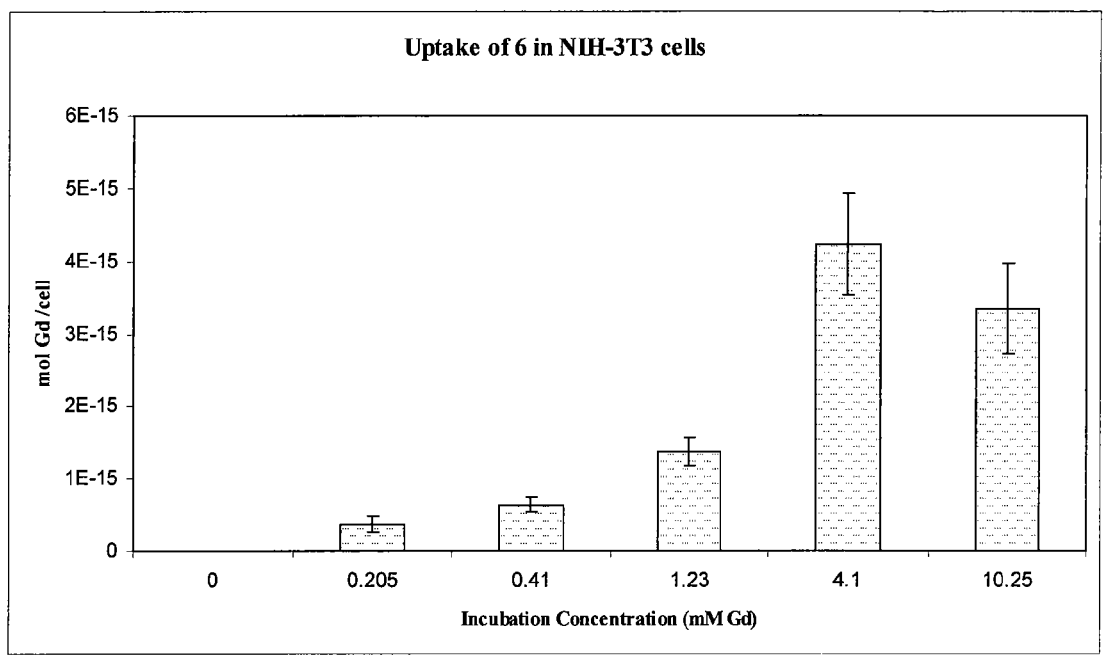
FIG. 10 shows uptake of 6 in NIH-3T3 cells.

Viability analysis revealed no change in viability of treated cells up to 10.25 mM. There was no difference in cell count between samples indicating that there were not damaged cells rinsed away during sample processing (FIG. 9). Gadolinium labeling analysis demonstrated a concentration dependant uptake of 6 and an apparent saturation level above 4 mM Gd(III) concentration, 0.57 mM agent concentration (FIG. 10).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in relevant fields, are intended to be within the scope of the following claims.

The invention claimed is:
1. A composition comprising at least one MR contrast agent selected from the group consisting of
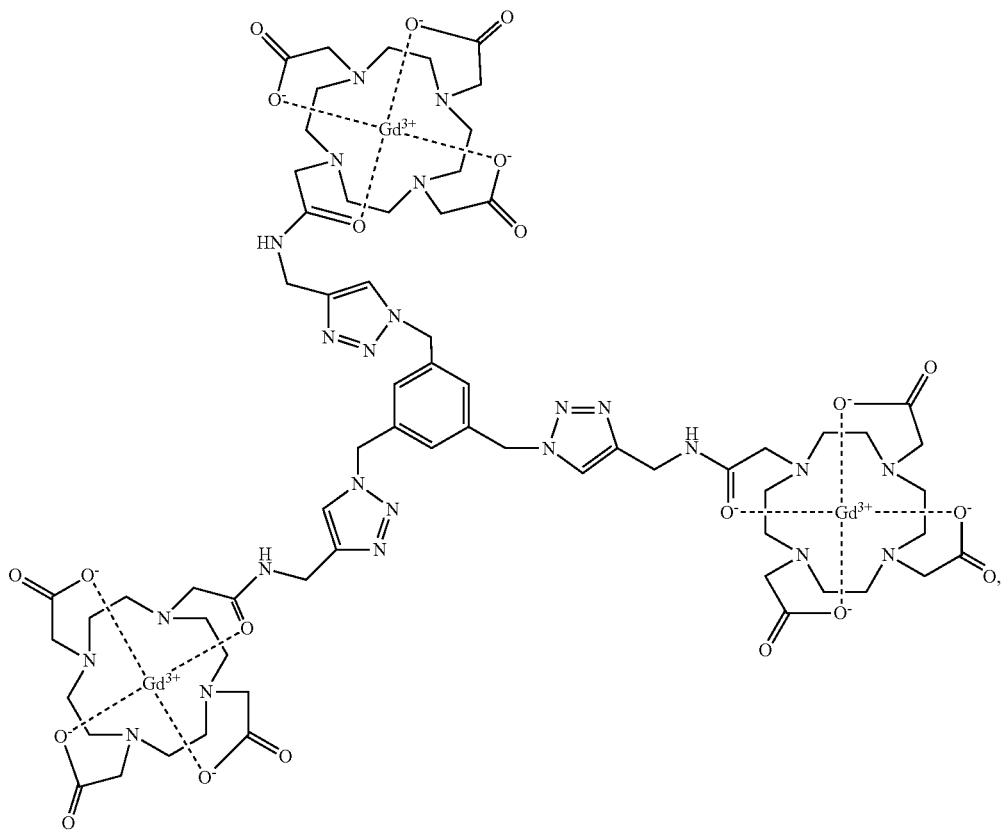
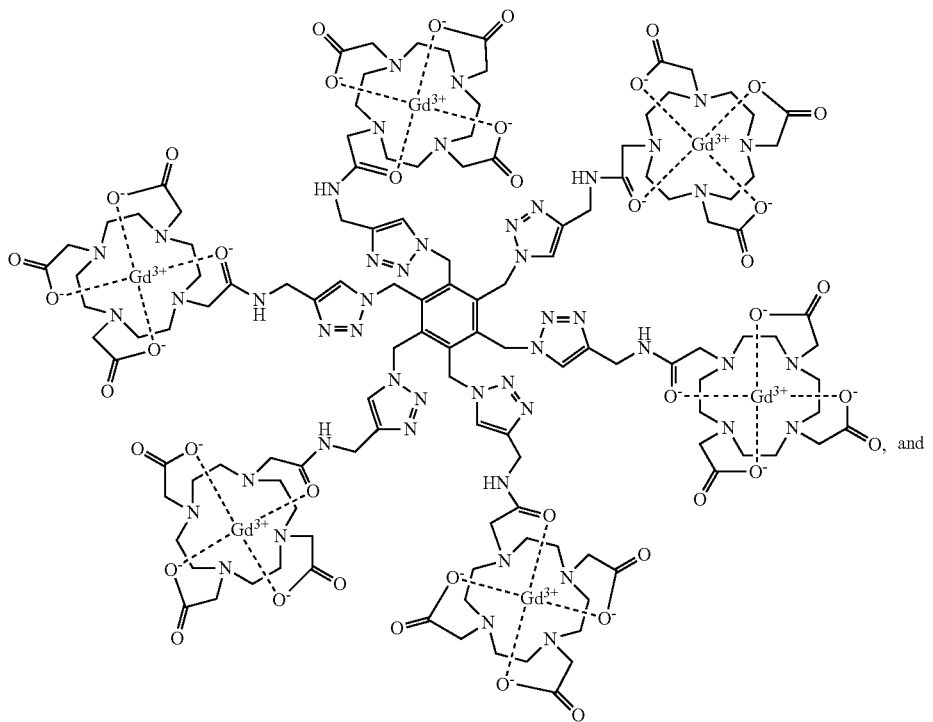

-continued
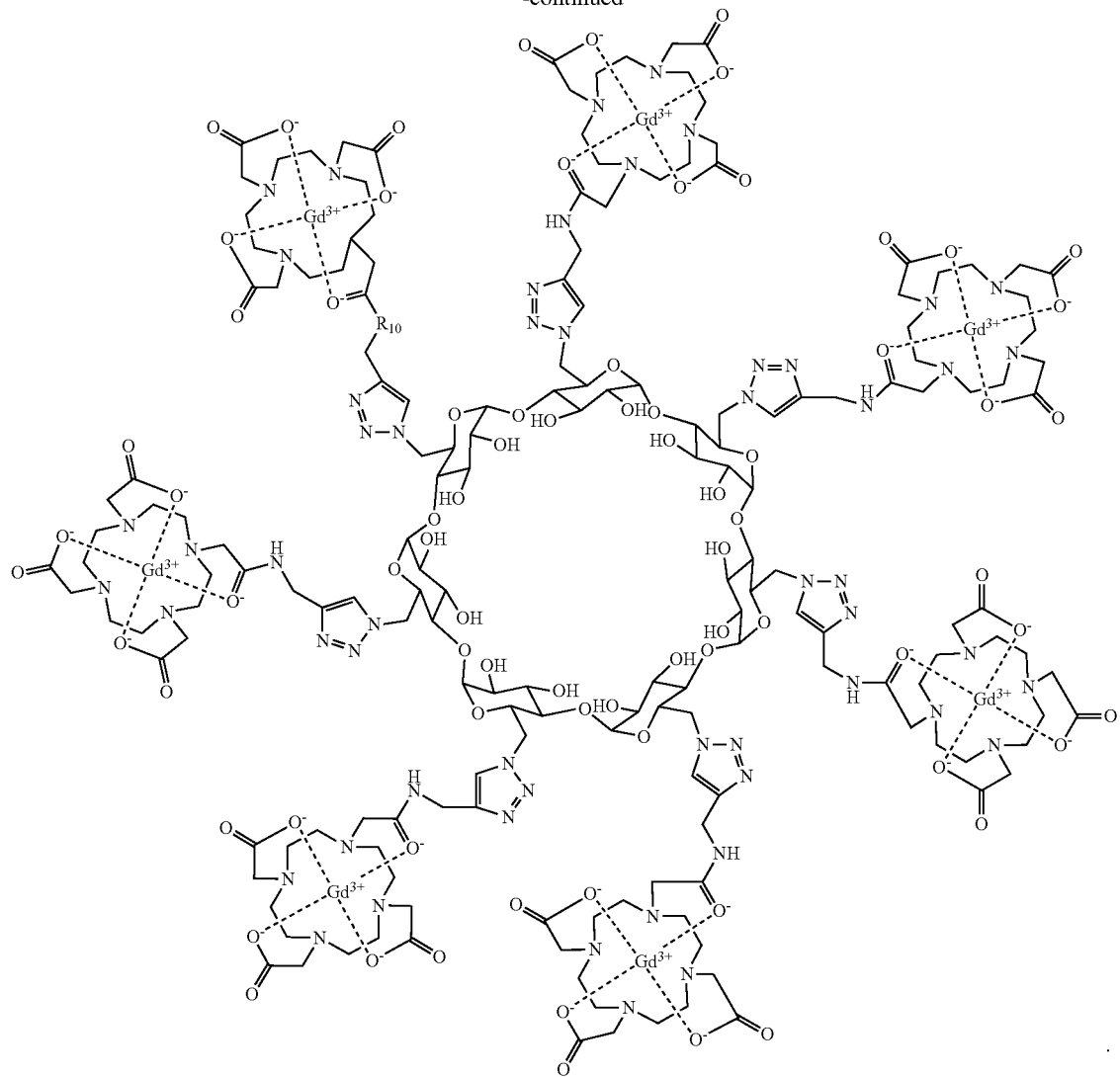
2. A method for imaging comprising administering a composition of claim 1 to a cell, tissue, or organism and detecting said contrasting agent.
* * * * *